(12) United States Patent
Gore et al.

(10) Patent No.: US 8,754,129 B2
(45) Date of Patent: Jun. 17, 2014

(54) CRYSTALLINE VORINOSTAT FORM VI

(75) Inventors: Vinayak Gore, Maharashtra (IN);
Madhukar Patil, Maharashtra (IN);
Rahul Bhalerao, Maharashtra (IN);
Hemant Mande, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 0 days.

(21) Appl. No.: 13/131,229

(22) PCT Filed: Nov. 25, 2009

(86) PCT No.: PCT/GB2009/051596
§ 371 (c)(1),
(2), (4) Date: Jul. 12, 2011

(87) PCT Pub. No.: WO2010/061219
PCT Pub. Date: Jun. 3, 2010

(65) Prior Publication Data
US 2011/0263713 A1 Oct. 27, 2011

(30) Foreign Application Priority Data
Nov. 26, 2008 (IN) .......................... 2057/KOL/2008

(51) Int. Cl.
*A01N 37/18* (2006.01)
*C07D 215/00* (2006.01)

(52) U.S. Cl.
USPC ........................................ 514/616; 564/155

(58) Field of Classification Search
None
See application file for complete search history.

(56) References Cited

U.S. PATENT DOCUMENTS

| | | | |
|---|---|---|---|
| 5,369,108 | A | 11/1994 | Breslow et al. |
| 6,497,820 | B1 | 12/2002 | Goetzinger et al. |
| 2004/0122101 | A1 | 6/2004 | Miller et al. |
| 2008/0132575 | A1 | 6/2008 | Wong |
| 2009/0223286 | A1 | 9/2009 | Singh et al. |
| 2011/0269838 | A1 | 11/2011 | Gore et al. |

FOREIGN PATENT DOCUMENTS

| | | |
|---|---|---|
| CA | 2671976 | 9/2003 |
| CA | 2663614 | 4/2008 |
| CA | 2712858 | 8/2009 |
| EP | 1541549 | 6/2005 |
| IN | 2057KOL2008 | 11/2009 |
| JP | H11-501025 | 1/1999 |
| JP | 2000-510472 | 8/2000 |
| JP | 2003-514904 | 4/2003 |
| JP | 2003-226680 | 8/2003 |
| JP | 2008-519081 | 6/2008 |
| WO | WO 2005018578 | 3/2005 |
| WO | WO 2006127319 | 11/2006 |
| WO | WO 2009077784 | 6/2009 |
| WO | WO 2009098515 | 8/2009 |
| WO | WO 2009111998 | 9/2009 |
| WO | WO 2010043904 | 4/2010 |
| WO | WO 2010061220 | 6/2010 |
| WO | WO 2011061545 | 5/2011 |

OTHER PUBLICATIONS

Remington's Pharmaceutical Sciences, (p. 382, 2006).*
Stowell J. C. et al., "The Synthesis of N-Hydroxy-N-phenyloctanediamide and Its Inhibitory Effect on Proliferation of AXC Rat Prostate Cancer Cells", Journal of Medicinal Chemistry, American Chemical Society, Washington, US, vol. 38, No. 8, Mar. 15, 1995, pp. 1411-1413.
International Search Report PCT/GB2009/051596 dated Jun. 24, 2010 (3 pgs.).
Du, et al. "High Turbulence Liquid Chromatography Online Extraction and Tandem Mass Spectrometry for the Simultaneous Determination of Suberoylanilide Hydroxamic Acid and its Two Metabolites in Human Serum", Rapid Communications in Mass Spectrometry, 2005, vol. 19, pp. 1779-1787.
Gediya, et al., "A New Simple and High-Yield Synthesis of Suberoylanilide Hydroxamic Acid and Its Inhibitory Effect Alone or in Combination with Retinoids on Proliferation of Human Prostate Cancer Cells", J Med Chem, 2005, vol. 48, pp. 5047-5051.
Mai, et al., "A New Facile and Expeditious Synthesis of N-Hydroxy-N1-Phenyloctanediamide, A Potent Inducer of Terminal Cytodifferentiation", OPPI Briefs, 2001, vol. 33(4), pp. 391-394.
Marks, et al., "Histone Deacetylase Inhibitors: Inducers of Differentiation or Apoptosis of Transformed Cells", J Nat Cancer Inst, 2000, vol. 92(15), pp. 1210-1216.
Parise, et al., "A liquid chromatography-electrospray ionization tandem mass spectrometric assay for quantitation of the histone deacetylase inhibitor, vorinostat (suberoylanilide hydroxamicacid, SAHA), and its metabolites in human serum", J Chromatography B, 2006, vol. 840, pp. 108-115.

(Continued)

*Primary Examiner* — Anna Pagonakis
(74) *Attorney, Agent, or Firm* — Fulbright & Jaworski LLP; Scott D. Rothenberger

(57) ABSTRACT

The present invention relates to crystalline forms of the active pharmaceutical ingredient vorinostat, processes for their preparation and their use in pharmaceutical compositions. Formula (I).

(I)

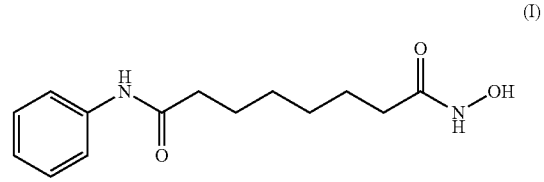

7 Claims, 3 Drawing Sheets

(56) References Cited

OTHER PUBLICATIONS

Patel, et al., "Simultaneous determination of decitabine and vorinostat (Suberoylanalide hydroxamic acid, SAHA) by liquid chromatography tandem mass spectrometry for clinical studies", J Chromatography B, 2008, vol. 863, pp. 19-25.

Prescribing information for Zolinza, Jul. 2008, 10 pages.
Wise, et al., "Assessment of Development Toxicity of Vorinostat, A Histone Deacetylase Inhibitor, in Sprague-Dawley Rats and Dutch Belted Rabbits—Birth Defects Research, 2007, part B, vol. 80, pp. 57-68". (XP-002529072).
www.Geosci.ipfw.edu, "Some Background about X-Ray Diffraction", accessed Nov. 28, 2012, 3 pages.

* cited by examiner

CRYSTALLINE VORINOSTAT FORM VI

CROSS-REFERENCE TO RELATED APPLICATION(s)

This application is a Section 371 National Stage Application of International No. PCT/GB2009/051596, filed 25 Nov. 2009 and published as WO 2010/061219 A3 on 3 Jun. 2010, which claims priority from the IN Patent Application No. 2057/KOL/2008, filed 26 Nov. 2008, the contents of which are incorporated herein in their entirety for all purposes.

FIELD OF THE INVENTION

The present invention relates to crystalline forms of the active pharmaceutical ingredient vorinostat, processes for their preparation and their use in pharmaceutical compositions.

BACKGROUND OF THE INVENTION

The manufacturing process for many pharmaceuticals is hindered by the fact that the organic compound, which is the active ingredient, has handling difficulties during the manufacturing process and may impart undesirable properties to the final drug or dosage form. In addition it can be difficult to control the polymorphic form of the active pharmaceutical ingredient throughout the manufacturing process.

For pharmaceuticals in which the active ingredient can exist in more than one polymorphic form, it is particularly important to ensure that the manufacturing process for the active ingredient affords a single, pure polymorph with a consistent level of polymorphic purity. If the manufacturing process leads to a polymorph with varying degrees of polymorphic purity and/or where the process does not control polymorphic interconversion, serious problems in dissolution and/or bioavailability can result in the finished pharmaceutical composition comprising the active ingredient.

Vorinostat, represented by structural formula (I) and chemically named as N-hydroxy-N'-phenyl-octanediamide or suberoylanilide hydroxamic acid (SAHA), is a member of a larger class of compounds that inhibit histone deacetylases (HDAC). Histone deacetylase inhibitors (HDI) have a broad spectrum of epigenetic activities and vorinostat is marketed, under the brand name Zolinza®, for the treatment of a type of skin cancer called cutaneous T-cell lymphoma (CTCL). Vorinostat is approved to be used when the disease persists, gets worse, or comes back during or after treatment with other medicines. Vorinostat has also been used to treat Sézary's disease and, in addition, possesses some activity against recurrent glioblastoma multiforme.

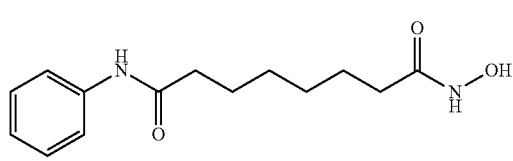

(I)

Vorinostat was first described in U.S. Pat. No. 5,369,108, but no polymorphic data was mentioned. Five crystalline forms of vorinostat, designated forms I to V respectively, were disclosed in documents US 2004/0122101 and WO 2006/127319. However, the five forms disclosed in these documents suffer from several disadvantages which do not make them ideal forms for pharmaceutical development. In particular, the disadvantages associated with the prior art forms I to V include discolouration, polymorphic impurities and instability. The prior art processes to prepare forms I to V, and in particular form III, suffer from the disadvantages of being inconsistent and difficult to reproduce, and they produce polymorphically impure products. The prior art processes are particularly inconvenient for large scale production.

If crystalline forms are made with polymorphic impurities, this causes instability and it can accelerate significant interconversion to another polymorphic form. Therefore it is crucial to produce crystalline forms with very high polymorphic purity to avoid this interconversion.

In view of the importance acquired by vorinostat for the treatment of cancer, there is a great need for developing an alternative, relatively simple, economical and commercially feasible process for the synthesis of vorinostat crystalline forms with commercially acceptable yield, high polymorphic purity and polymorphic stability.

OBJECT OF THE INVENTION

Therefore an object of the present invention is to provide a new polymorphic form of vorinostat, which is convenient to manufacture, and which has improved properties suitable for formulation development and as a marketed pharmaceutical composition. An additional objective is to improve existing processes to prepare known polymorphs of vorinostat and to improve the polymorphic purity of known polymorphs.

SUMMARY OF THE INVENTION

The present inventors have surprisingly developed a new polymorphic form of vorinostat, designated as form VI, with improved properties which circumvent the problems associated with the polymorphic forms reported in the prior art as described above.

The present inventors have also developed convenient processes for the preparation of vorinostat form III and novel vorinostat form VI under conditions which are very reproducible and produce vorinostat form III and vorinostat form VI in very high polymorphic purity.

Therefore, in a first aspect of the present invention there is provided a crystalline vorinostat form VI, characterised by an XRPD spectrum comprising three or more (preferably four or more, preferably five or more, preferably six or more, preferably seven or more, preferably eight or more, preferably nine or more, preferably ten or more, preferably twelve or more, preferably fifteen or more, or preferably all seventeen) of the following degrees 2θ peaks: 5.01, 7.50, 9.23, 9.92, 10.51, 12.46, 14.90, 17.32, 19.35, 19.86, 22.36, 23.85, 24.20, 24.74, 25.81, 26.93, 27.85±0.2 degrees 2θ. Preferably the crystalline vorinostat form VI according to the first aspect of the present invention has an XRPD spectrum substantially as shown in FIG. 1.

The crystalline vorinostat form VI according to the first aspect of the present invention may be further characterised by a differential scanning calorimetry (DSC) trace with endothermic peaks at about 148.2±2.0° C. and about 163.5±2.0° C., preferably with endothermic peaks at about 148.18±2.0° C. and about 163.46±2.0° C. Preferably the crystalline vorinostat form VI according to the first aspect of the present invention has a DSC trace substantially as shown in FIG. 2.

Preferably the crystalline vorinostat form VI according to the first aspect of the present invention has a TGA trace substantially as shown in FIG. 3.

In a second aspect of the present invention there is provided a process for preparing crystalline vorinostat form VI, comprising the steps of:
(a) mixing vorinostat, or a salt thereof, in an organic solvent and an aqueous solution of ammonia; and
(b) isolating the vorinostat form VI from the mixture.

Preferably, the organic solvent is selected from an alcohol, a nitrile, an ester, a ketone, an amide or mixtures thereof.

Preferably, the organic solvent is an alcohol, preferably a straight chain, branched or cyclic $C_1$ to $C_6$ alcohol. More preferably, the alcohol is selected from methanol, isopropanol or mixtures thereof.

Preferably, the organic solvent is a ketone, preferably selected from acetone, methyl ethyl ketone, methyl isobutyl ketone, diethyl ketone or mixtures thereof.

Preferably, the organic solvent is an amide, preferably selected from N,N-dimethylformamide, N,N-dimethylacetamide or mixtures thereof.

Preferably, the organic solvent is an ester, preferably selected from ethyl acetate, methyl acetate or mixtures thereof.

Preferably, the organic solvent is a nitrile, preferably selected from acetonitrile, propionitrile or mixtures thereof.

Preferably, the concentration of the aqueous solution of ammonia used in the process of the second aspect of the present invention is between 10 to 50% (w/w). More preferably, the concentration of the aqueous solution of ammonia is about 25% (w/w).

Preferably, the ratio of organic solvent:aqueous ammonia used in step (a) is from 5:1 to 3:1, preferably the ratio of organic solvent:aqueous ammonia used in step (a) is about 10:3.

Preferably, for each gram of vorinostat about 30-50 ml of solvent (organic solvent and aqueous ammonia together) are used in step (a), preferably about 35-50 ml of solvent, preferably about 39 ml of solvent.

Preferably, in the process according to the second aspect of the present invention, the mixture is heated to dissolve the vorinostat or its salt. Preferably, the mixture is heated between 40 to 100° C., more preferably at about 60° C.

Preferably, in the process according to the second aspect of the present invention, the mixture is cooled before isolation of the vorinostat form VI. Preferably, the mixture is cooled to between 5 to 30° C., more preferably to about 25° C.

In a third aspect of the present invention there is provided crystalline vorinostat form VI, as prepared by a process according to the second aspect of the present invention.

Preferably, the crystalline vorinostat form VI according to the first or third aspect of the present invention comprises less than 10% of vorinostat in other polymorphic forms, preferably less than 5%, more preferably less than 1%, even more preferably less than 0.5%, and most preferably less than 0.2%, preferably as measured by XRPD or DSC, preferably as measured by XRPD.

In a fourth aspect of the present invention there is provided crystalline vorinostat form VI, comprising less than 10% of vorinostat in other polymorphic forms, preferably comprising less than 5% of vorinostat in other polymorphic forms, more preferably comprising less than 1% of vorinostat in other polymorphic forms, even more preferably comprising less than 0.5% of vorinostat in other polymorphic forms, and most preferably comprising less than 0.2% of vorinostat in other polymorphic forms, preferably as measured by XRPD or DSC, preferably as measured by XRPD.

Preferably, the crystalline vorinostat form VI according to the first, third or fourth aspect of the present invention has a chemical purity of at least 95%, more preferably at least 98%, more preferably at least 99%, more preferably at least 99.5%, even more preferably at least 99.8%, and most preferably at least 99.9%, preferably as measured by HPLC.

Preferably, the crystalline vorinostat form VI according to the first, third or fourth aspect of the present invention can be used to prepare other polymorphic forms of vorinostat, including known polymorphic forms of vorinostat such as form III.

Preferably, the crystalline vorinostat form VI according to the first, third or fourth aspect of the present invention is suitable for use in medicine, preferably for treating cancer, preferably for treating skin cancer, preferably for treating cutaneous T-cell lymphoma (CTCL).

In a fifth aspect of the present invention there is provided a pharmaceutical composition, comprising the crystalline vorinostat form VI according to the first, third or fourth aspect of the present invention. Preferably, the pharmaceutical composition further comprises one or more pharmaceutically acceptable excipients. Preferably, the pharmaceutical composition according to the fifth aspect of the present invention is suitable for treating cancer, preferably for treating skin cancer, preferably for treating cutaneous T-cell lymphoma (CTCL).

In a sixth aspect of the present invention there is provided the use of the crystalline vorinostat form VI according to the first, third or fourth aspect of the present invention or the use of the pharmaceutical composition according to the fifth aspect of the present invention, in the manufacture of a medicament for treating cancer. Preferably, the medicament is for the treatment of skin cancer, more preferably for the treatment of cutaneous T-cell lymphoma (CTCL).

In a seventh aspect of the present invention there is provided a method of treating cancer, comprising administering to a patient in need thereof a therapeutically effective amount of the crystalline vorinostat form VI according to the first, third or fourth aspect of the present invention or a therapeutically effective amount of the pharmaceutical composition according to the fifth aspect of the present invention. Preferably, the method is for the treatment of skin cancer, more preferably for the treatment of cutaneous T-cell lymphoma (CTCL). Preferably, the patient is a mammal, preferably a human.

In an eighth aspect of the present invention there is provided a process for the preparation of crystalline vorinostat form III, comprising:
(a) mixing vorinostat form VI in either ethanol or acetonitrile, and aqueous ammonia to form a slurry; and
(b) isolating the vorinostat form III formed.

As used herein throughout the specification and claims, the term "vorinostat form III" refers to the vorinostat form III as described and characterised in US 2004/0122101 and WO 2006/127319. Preferably the vorinostat form III is characterised by an XRPD spectrum comprising three or more (preferably four or more, preferably five or more, preferably six or more, preferably seven or more, preferably eight or more, preferably nine or more, preferably ten or more, preferably twelve or more, preferably fifteen or more, preferably twenty or more, or preferably all twenty-two) of the following degrees 2θ peaks: 10.1, 12.1, 13.8, 15.1, 17.7, 18.5, 18.8, 19.6, 20.2, 20.9, 21.7, 23.8, 24.5, 25.0, 25.4, 26.1, 26.8, 35.6, 37.1, 40.9, 42.4, 44.8±0.2 degrees 2θ, when measured using a Siemens D500 Automated Powder Diffractometer equipped with a copper radiation source with a wavelength of 1.54 Å. Preferably the vorinostat form III is characterised by a differential scanning calorimetry (DSC) trace with endothermic peaks at about 123.5° C.±2.0° C. and about 148.9° C.±2.0° C., when measured using a Perkin Elmer instrument, over a temperature range of from 50° C. to 30° C. above the observed melting temperature, at a heating rate of 10° C./min, using a standard aluminium pan and cover as crucible.

Preferably, the concentration of the aqueous ammonia used in the process of the eighth aspect of the present invention is between 10 to 50% (w/w). More preferably, the concentration of the aqueous ammonia is about 25% (w/w).

Preferably, the ratio of ethanol or acetonitrile:aqueous ammonia used in step (a) is from 5:1 to 3:1, preferably the ratio of ethanol or acetonitrile:aqueous ammonia used in step (a) is about 10:3.

Preferably, for each gram of vorinostat about 10-30 ml of solvent (organic solvent and aqueous ammonia together) are used in step (a), preferably about 10-25 ml of solvent, preferably about 19.5 ml of solvent.

Preferably, the slurry is heated to dissolve the vorinostat, preferably the slurry is heated between 40 to 100° C., more preferably at about 60° C.

Preferably, the slurry is cooled before isolation of the vorinostat form III, more preferably the slurry is cooled to between 5 to 30° C., most preferably to about 25° C.

In a ninth aspect of the present invention there is provided crystalline vorinostat form III, as prepared by a process according to the eighth aspect of the present invention.

Preferably, the crystalline vorinostat form III according to the ninth aspect of the present invention comprises less than 2% of vorinostat in other polymorphic forms, preferably less than 1%, more preferably less than 0.5%, even more preferably less than 0.2%, and most preferably less than 0.1%, preferably as measured by XRPD or DSC, preferably as measured by XRPD.

In a tenth aspect of the present invention there is provided crystalline vorinostat form III, comprising less than 2% of vorinostat in other polymorphic forms, preferably comprising less than 1% of vorinostat in other polymorphic forms, more preferably comprising less than 0.5% of vorinostat in other polymorphic forms, even more preferably comprising less than 0.2% of vorinostat in other polymorphic forms, and most preferably comprising less than 0.1% of vorinostat in other polymorphic forms, preferably as measured by XRPD or DSC, preferably as measured by XRPD.

Preferably, the crystalline vorinostat form III according to the ninth or tenth aspect of the present invention has a chemical purity of at least 95%, more preferably at least 98%, more preferably at least 99%, more preferably at least 99.5%, even more preferably at least 99.8%, and most preferably at least 99.9%, preferably as measured by HPLC.

Preferably, the crystalline vorinostat form III according to the ninth or tenth aspect of the present invention is suitable for use in medicine, preferably for treating cancer, preferably for treating skin cancer, preferably for treating cutaneous T-cell lymphoma (CTCL).

In an eleventh aspect of the present invention there is provided a pharmaceutical composition, comprising the crystalline vorinostat form III according to the ninth or tenth aspect of the present invention. Preferably, the pharmaceutical composition further comprises one or more pharmaceutically acceptable excipients. Preferably, the pharmaceutical composition according to the eleventh aspect of the present invention is suitable for treating cancer, preferably for treating skin cancer, preferably for treating cutaneous T-cell lymphoma (CTCL).

In a twelfth aspect of the present invention there is provided the use of the crystalline vorinostat form III according to the ninth or tenth aspect of the present invention or the use of the pharmaceutical composition according to the eleventh aspect of the present invention, in the manufacture of a medicament for treating cancer. Preferably, the medicament is for the treatment of skin cancer, more preferably for the treatment of cutaneous T-cell lymphoma (CTCL).

In a thirteenth aspect of the present invention there is provided a method of treating cancer, comprising administering to a patient in need thereof a therapeutically effective amount of the crystalline vorinostat form III according to the ninth or tenth aspect of the present invention or a therapeutically effective amount of the pharmaceutical composition according to the eleventh aspect of the present invention. Preferably, the method is for the treatment of skin cancer, more preferably for the treatment of cutaneous T-cell lymphoma (CTCL). Preferably, the patient is a mammal, preferably a human.

BRIEF DESCRIPTION OF THE ACCOMPANYING FIGURES

DETAILED DESCRIPTION OF THE INVENTION

Figure 1:
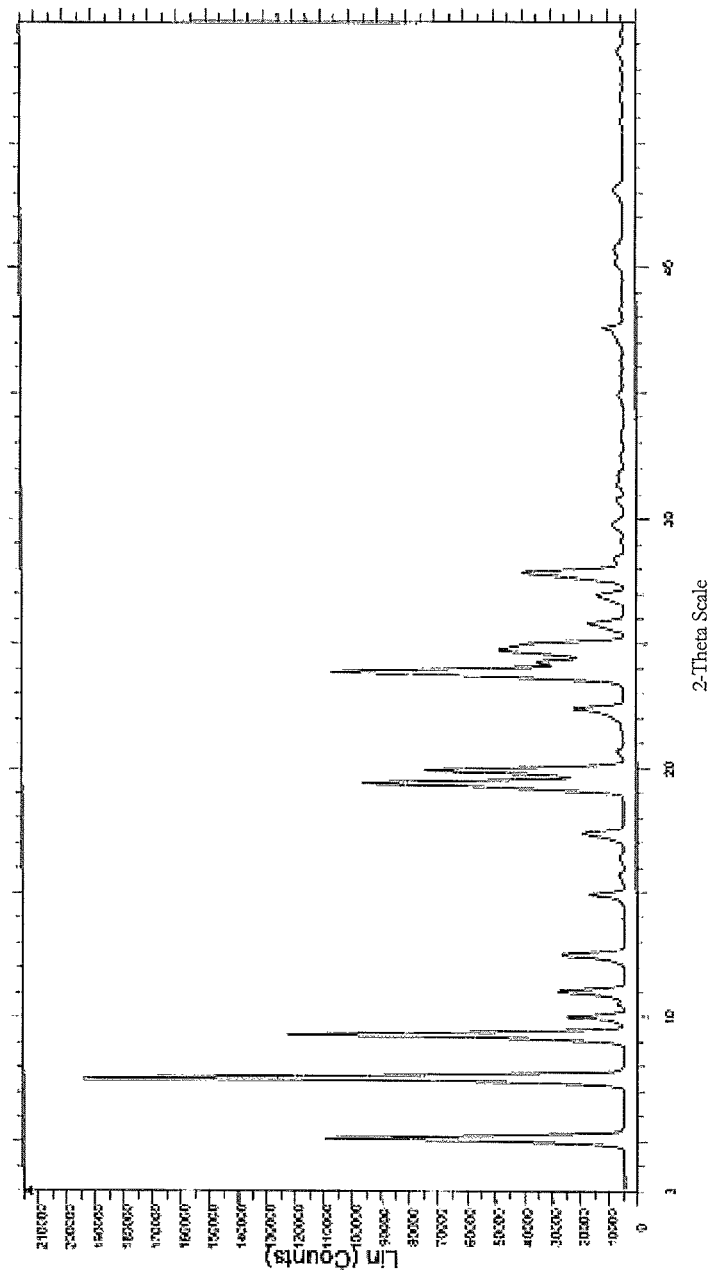
FIG. 1 shows an X-ray powder diffraction (XRPD) spectrum of vorinostat form VI.

As outlined above, the present invention provides a new crystalline form of vorinostat, form VI, which is non-hygroscopic, polymorphically pure and stable and has beneficial properties which avoid the problems associated with prior art forms.

In addition, a new process has been developed for the preparation of crystalline vorinostat form III, which can produce the form III in very high polymorphic purity.

Preferred embodiments of the processes according to the present invention are described below.

In a preferred embodiment of the process of the second aspect of the present invention, vorinostat is mixed with one or more organic solvents and an aqueous ammonia solution (~25% w/w). The resulting suspension is preferably heated at about 60° C. for about one hour under stirring. Preferably, the clear reaction mixture is then cooled to about 25° C. and filtered. The crystalline vorinostat form VI obtained is preferably dried at about 60° C. under vacuum until a constant weight is obtained.

Preferably, the organic solvent is selected from an alcohol, a nitrile, an ester, a ketone, an amide or mixtures thereof. Preferably, the organic solvent is an alcohol, preferably a straight chain, branched or cyclic $C_1$ to $C_6$ alcohol. More preferably, the alcohol is selected from methanol, isopropanol or mixtures thereof. Preferably, the organic solvent is a ketone, preferably selected from acetone, methyl ethyl ketone, methyl isobutyl ketone, diethyl ketone or mixtures thereof. Preferably, the organic solvent is an amide, preferably selected from N,N-dimethylformamide, N,N-dimethylacetamide or mixtures thereof. Preferably, the organic solvent is an ester, preferably selected from ethyl acetate, methyl acetate or mixtures thereof. Preferably, the organic solvent is a nitrile, preferably selected from acetonitrile, propionitrile or mixtures thereof.

The major advantages of this invention are the reproducible conditions of the process to obtain the novel polymorph and the polymorphic purity and stability of the vorinostat form VI.

The polymorphic form of the present invention also allows vorinostat to be easily purified and obtained in very high chemical purity.

In addition, the present inventors have surprisingly found that the novel crystalline vorinostat form VI can be conveniently used to prepare other known crystalline forms of vorinostat, such as form III, and particularly surprisingly, that the form III afforded is characterised by a very high polymorphic purity.

A preferred process for the preparation of vorinostat form III comprises mixing vorinostat form VI in ethanol (or acetonitrile) and aqueous ammonia, heating the slurry at about 60° C., cooling, and filtering the vorinostat form III formed. The vorinostat form III is then preferably dried to constant weight.

Preferably, the vorinostat form VI and form III obtained are dried until the moisture content falls below about 1%, preferably to below about 0.5%.

The pharmaceutical composition according to the fifth and eleventh aspect of the present invention can be a solution or a suspension, but is preferably a solid oral dosage form Preferred oral dosage forms in accordance with the invention include tablets, capsules and the like which, optionally, may be coated if desired. Tablets can be prepared by conventional techniques, including direct compression, wet granulation and dry granulation. Capsules are generally formed from a gelatine material and can include a conventionally prepared granulate of excipients in accordance with the invention.

The pharmaceutical composition according to the present invention typically comprises one or more conventional pharmaceutically acceptable excipient(s) selected from the group comprising a filler, a binder, a disintegrant, a lubricant and optionally further comprises at least one excipient selected from colouring agents, adsorbents, surfactants, film-formers and plasticizers.

If the solid pharmaceutical formulation is in the form of coated tablets, the coating may be prepared from at least one film-former such as hydroxypropyl methyl cellulose, hydroxypropyl cellulose or methacrylate polymers which optionally may contain at least one plasticizer such as polyethylene glycols, dibutyl sebacate, triethyl citrate, and other pharmaceutical auxiliary substances conventional for film coatings, such as pigments and fillers.

Preferably, the pharmaceutical compositions according to the present invention are in unit dosage form comprising vorinostat in an amount of from 1 mg to 500 mg, such that the amount of vorinostat administered is from 0.1 mg to 100 mg per kg per day.

Preferably, the pharmaceutical compositions according to the fifth and eleventh aspect of the present invention are for use in the treatment of cancer, preferably in the treatment of skin cancer, and most preferably in the treatment of cutaneous T-cell lymphoma (CTCL).

The details of the invention, its objects and advantages are illustrated below in greater detail by non-limiting examples.

EXAMPLES

All XRPD analyses were carried out on a Bruker D8 Advance instrument, equipped with a copper radiation source with a wavelength of 1.54 Å.

All DSC analyses were carried out on a Perkin Elmer instrument, over a temperature range of 25° C. to 250° C., at a heating rate of 10° C./min, using a closed aluminium pan with a pinhole as crucible.

All TGA analyses were carried out on a Perkin Elmer instrument, over a temperature range of 25° C. to 250° C., at a heating rate of 10° C./min, using an open ceramic pan as crucible.

All Drift IR analyses were carried out on a Perkin Elmer instrument, at a temperature of 25° C., using KBr.

Example 1

Preparation of Crystalline Vorinostat Form VI

Vorinostat (10 g) was charged to a reaction flask containing methanol (300 ml) and aqueous ammonia (~25% w/w, 90 ml) and the suspension was heated at 60° C. for one hour under stirring. The resultant clear solution was cooled to 25° C. and filtered to obtain a solid product, which was dried at 60° C. under vacuum until a constant weight was obtained.
Yield=7.5 g (75%)
Chemical purity≥99.9% (as measured by HPLC)

Example 2

Preparation of Crystalline Vorinostat Form VI

Vorinostat (10 g) was charged to a reaction flask containing acetone (300 ml) and aqueous ammonia (~25% w/w, 90 ml) and the suspension was heated at 60° C. for one hour under stirring. The resultant clear solution was cooled to 25° C. and filtered to obtain a solid product, which was dried at 60° C. under vacuum until a constant weight was obtained.
Yield=8.1 g (81%)
Chemical purity≥99.9% (as measured by HPLC)

Example 3

Preparation of Crystalline Vorinostat Form VI

Vorinostat (10 g) was charged to a reaction flask containing acetonitrile (300 ml) and aqueous ammonia (~25% w/w, 90 ml) and the suspension was heated at 60° C. for one hour under stirring. The resultant clear solution was cooled to 25° C. and filtered to obtain a solid product, which was dried at 60° C. under vacuum until a constant weight was obtained.
Yield=8.3 g (83%)
Chemical purity≥99.9% (as measured by HPLC)

Example 4

Preparation of Crystalline Vorinostat Form VI

Vorinostat (10 g) was charged to a reaction flask containing ethyl acetate (300 ml) and aqueous ammonia (~25% w/w, 90 ml) and the suspension was heated at 60° C. for one hour under stirring. The resultant clear solution was cooled to 25° C. and filtered to obtain a solid product, which was dried at 60° C. under vacuum until a constant weight was obtained.
Yield=7.8 g (78%)
Chemical purity≥99.9% (as measured by HPLC)

Example 5

Preparation of Crystalline Vorinostat Form VI

Vorinostat (10 g) was charged to a reaction flask containing N,N-dimethylformamide (300 ml) and aqueous ammonia (~25% w/w, 90 ml) and the suspension was heated at 60° C. for one hour under stirring. The resultant clear solution was cooled to 25° C. and filtered to obtain a solid product, which was dried at 60° C. under vacuum until a constant weight was obtained.

Yield=7.9 g (79%)

Chemical purity≥99.9% (as measured by HPLC)

Figure 2:
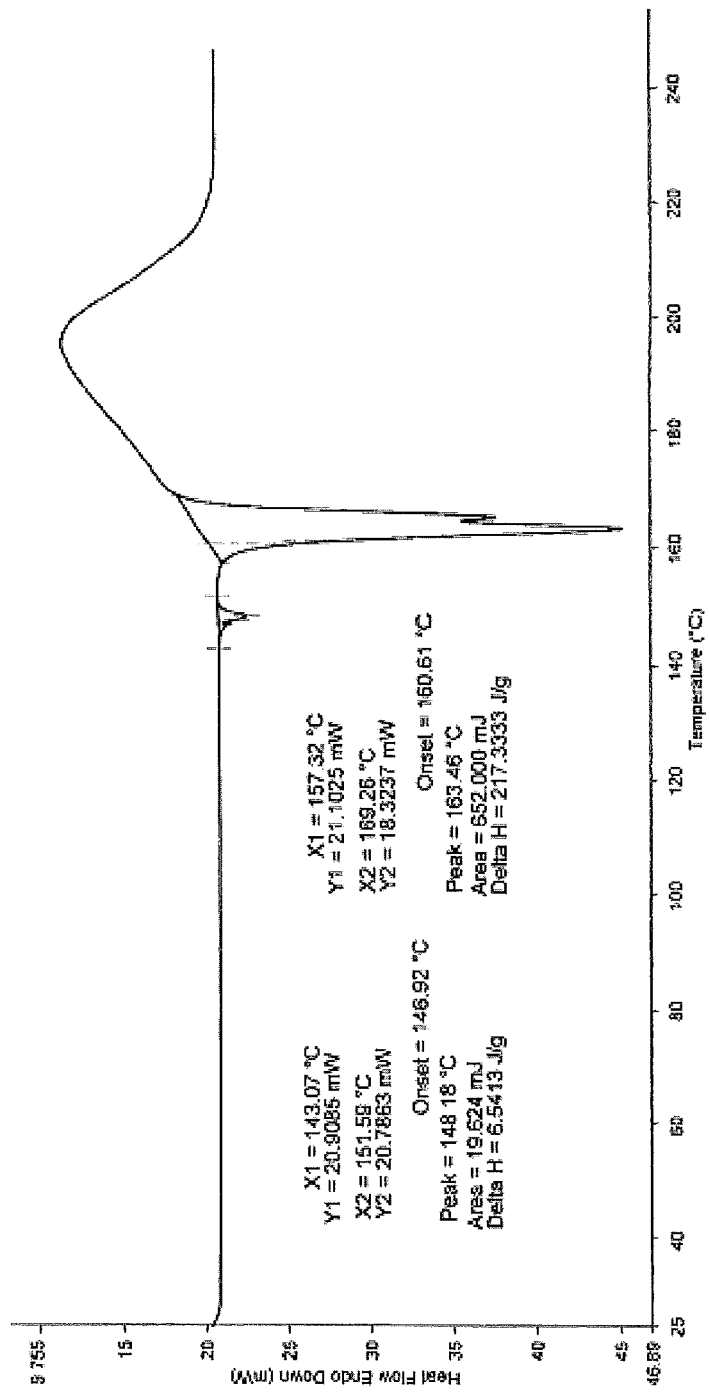
FIG. 2 shows a differential scanning calorimetry (DSC) trace of vorinostat form VI.
Figure 3:
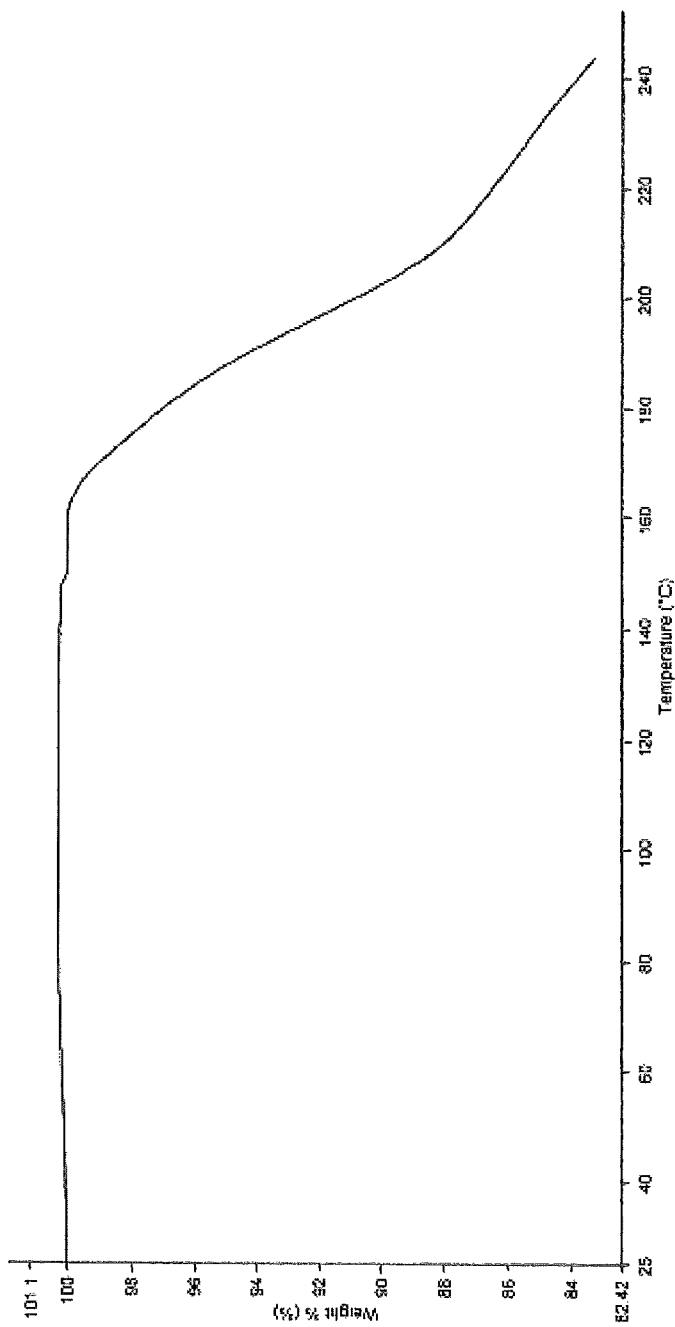
FIG. 3 shows a thermo-gravimetric analysis (TGA) trace of vorinostat form VI.

XRPD and DSC analysis data for the products obtained from examples 1 to 5 are shown in FIGS. 1 and 2 respectively and confirmed that the products obtained were a novel polymorph of vorinostat. TGA analysis data are shown in FIG. 3.

The novel polymorph obtained, crystalline form VI, was substantially pure polymorphically with no levels of other forms detected (>99.7% polymorphically pure). Specifically, the crystalline form VI prepared was free from polymorphic forms I and III as confirmed by Drift IR and free from polymorphic forms II, IV and V as confirmed by XRPD and DSC data.

The crystalline form VI was also found to be very stable polymorphically with no conversion over time to other polymorphs, when kept at a temperature of 40° C.±2° C. and a relative humidity of 75%±5% for 6 months.

Example 6

Preparation of Crystalline Vorinostat Form III

Vorinostat form VI (10 g) was charged to a reaction flask containing ethanol (150 ml) and aqueous ammonia (~25% w/w, 45 ml). The resulting suspension was heated at 60° C. for one hour under stirring. The reaction mixture was cooled to 25° C. and filtered. The solid product was dried at 60° C. under vacuum until a constant weight was obtained.

Yield=6.2 g (62%)

Chemical purity≥99.9% (as measured by HPLC)

Example 7

Preparation of Crystalline Vorinostat Form III

Vorinostat form VI (10 g) was charged to a reaction flask containing acetonitrile (150 ml) and aqueous ammonia (~25% w/w, 45 ml). The resulting suspension was heated at 60° C. for one hour under stirring. The reaction mixture was cooled to 25° C. and filtered. The solid product was dried at 60° C. under vacuum until a constant weight was obtained.

Yield=6.4 g (64%)

Chemical purity≥99.9% (as measured by HPLC)

$^1$H-NMR analysis of the products obtained from examples 6 and 7 indicated formation of vorinostat. XRPD and DSC analysis data confirmed that the products obtained were crystalline form III of vorinostat, in accordance with the data disclosed in US 2004/0122101 and WO 2006/127319.

The samples of crystalline vorinostat form III prepared in examples 6 and 7 were found to be substantially pure polymorphically with no levels of other forms detected (>99.7% polymorphically pure), as confirmed by XRPD and DSC data.

The samples of crystalline vorinostat form III prepared were also found to be very stable polymorphically with no conversion over time to other polymorphs, when kept at a temperature of 40° C.±2° C. and a relative humidity of 75%±5% for 6 months.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. Crystalline vorinostat form VI, characterised by an XRPD spectrum comprising fifteen or more of the following degrees 2θ peaks: 5.01, 7.50, 9.23, 9.92, 10.51, 12.46, 14.90, 17.32, 19.35, 19.86, 22.36, 23.85, 24.20, 24.74, 25.81, 26.93, 27.85 ±0.2 degrees 2θ.

2. Crystalline vorinostat form VI characterised by an XRPD spectrum comprising fifteen or more of the following degrees 2θ peaks: 5.01, 7.50, 9.23, 9.92, 10.51, 12.46, 14.90, 17.32, 19.35, 19.86, 22.36, 23.85, 24.20, 24.74, 25.81, 26.93, 27.85±0.2 degrees 2θ, characterised by a differential scanning calorimetry (DSC) trace with endothermic peaks at 48.2 ±2.0° C. and 163.5±2.0° C.

3. A process for preparing crystalline vorinostat form VI characterised by an XRPD spectrum comprising fifteen or more of the following degrees 2θ peaks: 5.01, 7.50, 9.23, 9.92, 10.51, 12.46, 14.90, 17.32, 19.35, 19.86, 22.36, 23.85, 24.20, 24.74, 25.81, 26.93, 27.85±0.2 degrees 2θ, comprising the steps of:
 (a) mixing vorinostat, or a salt thereof, in an organic solvent and an aqueous solution of ammonia; and
 (b) isolating the vorinostat form VI from the mixture.

4. A process according to claim 3, wherein the organic solvent is:
 (i) selected from an alcohol, a nitrile, an ester, a ketone, an amide or a mixture thereof; and/or
 (ii) an alcohol; and/or
 (iii) a straight chain, branched or cyclic $C_1$ to $C_6$ alcohol; and/or
 (iv) an alcohol selected from methanol, isopropanol or a mixture thereof; and/or
 (v) a ketone; and/or
 (vi) a ketone selected from acetone, methyl ethyl ketone, methyl isobutyl ketone, diethyl ketone or a mixture thereof; and/or
 (vii) an amide; and/or
 (viii) an amide selected from N,N-dimethylformamide, N,N-dimethylacetamide or a mixture thereof; and/or
 (ix) an ester; and/or
 (x) an ester selected from ethyl acetate, methyl acetate or a mixture thereof; and/or
 (xi) a nitrile; and/or
 (xii) a nitrile selected from acetonitrile, propionitrile or a mixture thereof.

5. A process according to claim 3, wherein:
 (i) the concentration of the aqueous solution of ammonia is between 10 to 50% (w/w); and/or
 (ii) the concentration of the aqueous solution of ammonia is about 25% (w/w); and/or
 (iii) in step (a) the mixture is heated to dissolve the vorinostat or its salt; and/or
 (iv) in step (a) the mixture is heated between 40 to 100° C. to dissolve the vorinostat or its salt; and/or
 (v) in step (a) the mixture is heated at about 60° C. to dissolve the vorinostat or its salt; and/or
 (vi) the mixture is cooled before isolation of the vorinostat form VI; and/or
 (vii) the mixture is cooled to between 5 to 30° C. before isolation of the vorinostat form VI; and/or
 (viii) the mixture is cooled to about 25° C. before isolation of the vorinostat form VI.

6. Crystalline vorinostat form VI characterised by an XRPD spectrum comprising fifteen or more of the following degrees 2θ peaks: 5.01, 7.50, 9.23, 9.92, 10.51, 12.46, 14.90, 17.32, 19.35, 19.86, 22.36, 23.85, 24.20, 24.74, 25.81, 26.93, 27.85±0.2 degrees 2θ, as prepared by a process according to claim 3.

7. A pharmaceutical composition, comprising the crystalline vorinostat form VI character by an XRPD spectrum comprising fifteen or more of the following degrees 2θ peaks: 5.01, 7.50, 9.23, 9.92, 10.51, 12.46, 14.90, 17.32, 19.35, 19.86, 22.36, 23.85, 24.20, 24.74, 25.81, 26.93, 27.85±0.2 degrees 2θ and one or more pharmaceutically acceptable excipients.

* * * * *